(12) United States Patent
Harale et al.

(10) Patent No.: US 11,279,891 B2
(45) Date of Patent: Mar. 22, 2022

(54) SYSTEMS AND PROCESSES FOR DIRECT CRUDE OIL UPGRADING TO HYDROGEN AND CHEMICALS

(71) Applicant: Saudi Arabian Oil Company, Dhahran (SA)

(72) Inventors: Aadesh Harale, Dhahran (SA); Ibrahim Abba, Dhahran (SA); Ahmad Khowaiter, Dhahran (SA); Abdennour Bourane, Dhahran (SA); Aqil Jamal, Dhahran (SA); Mourad Younes, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 125 days.

(21) Appl. No.: 16/810,596

(22) Filed: Mar. 5, 2020

(65) Prior Publication Data

US 2021/0277318 A1  Sep. 9, 2021

(51) Int. Cl.

| | |
|---|---|
| *B01J 8/24* | (2006.01) |
| *C01B 3/34* | (2006.01) |
| *C10G 65/12* | (2006.01) |
| *C10G 65/14* | (2006.01) |
| *C10G 69/00* | (2006.01) |
| *C01B 32/50* | (2017.01) |
| *B01D 3/06* | (2006.01) |
| *B01D 19/00* | (2006.01) |
| *B01J 8/18* | (2006.01) |
| *B01J 19/24* | (2006.01) |
| *C01B 3/36* | (2006.01) |
| *C01B 3/48* | (2006.01) |
| *C07C 6/12* | (2006.01) |
| *C07C 51/14* | (2006.01) |
| *C10G 2/00* | (2006.01) |

(52) U.S. Cl.
CPC ............... *C10G 69/00* (2013.01); *B01D 3/06* (2013.01); *B01D 19/0057* (2013.01); *B01J 8/1827* (2013.01); *B01J 8/24* (2013.01); *B01J 19/245* (2013.01); *B01J 19/2445* (2013.01); *C01B 3/34* (2013.01); *C01B 3/36* (2013.01); *C01B 3/48* (2013.01); *C01B 32/50* (2017.08); *C07C 6/126* (2013.01); *C07C 51/14* (2013.01); *C10G 2/32* (2013.01); *C10G 2/344* (2013.01); *B01J 2208/00893* (2013.01); *B01J 2219/0004* (2013.01); *B01J 2219/00038* (2013.01); *C01B 2203/0233* (2013.01); *C01B 2203/0244* (2013.01); *C01B 2203/0255* (2013.01); *C01B 2203/0283* (2013.01); *C01B 2203/1241* (2013.01); *C10G 2300/1044* (2013.01); *C10G 2300/1055* (2013.01); *C10G 2400/20* (2013.01); *C10G 2400/30* (2013.01)

(58) Field of Classification Search
CPC ..... B01J 8/24; B01J 2219/00006; C01B 3/34; C10G 65/12; C10G 65/14; C10G 67/0436; C10G 69/126; C10G 2300/1044; C10G 2300/1055; C10G 2400/20; C10G 2400/30

See application file for complete search history.

(56) References Cited

U.S. PATENT DOCUMENTS

| | | |
|---|---|---|
| 3,755,143 A | 8/1973 | Hosoi et al. |
| 3,856,659 A | 12/1974 | Owen |
| 4,090,949 A | 5/1978 | Owen et al. |
| 4,134,824 A | 1/1979 | Kamm et al. |
| 4,264,435 A | 4/1981 | Read, Jr. et al. |
| 4,297,203 A | 10/1981 | Ford et al. |
| 4,527,003 A | 7/1985 | Okamoto et al. |
| 4,587,011 A | 5/1986 | Okamoto et al. |
| 4,655,904 A | 4/1987 | Okamoto et al. |
| 4,725,349 A | 2/1988 | Okamoto et al. |
| 4,830,728 A | 5/1989 | Herbst et al. |
| 4,992,160 A | 2/1991 | Long et al. |
| 5,904,837 A | 5/1999 | Fujiyama |
| 5,906,728 A | 5/1999 | Iaccino et al. |
| 5,951,850 A | 9/1999 | Ino et al. |
| 6,033,555 A | 3/2000 | Chen et al. |
| 6,190,533 B1 | 2/2001 | Bradow et al. |
| 6,210,562 B1 | 4/2001 | Xie et al. |
| 6,656,346 B2 | 12/2003 | Ino et al. |

(Continued)

FOREIGN PATENT DOCUMENTS

| | | |
|---|---|---|
| CN | 105194995 A | 12/2015 |
| FR | 2990695 A1 | 11/2013 |
| WO | 2016059568 A1 | 4/2016 |

OTHER PUBLICATIONS

International Search Report and Written Opinion of PCT Application No. PCT/US2021/020982 dated Jun. 8, 2021: pp. 1-12.

*Primary Examiner* — Randy Boyer
(74) *Attorney, Agent, or Firm* — Bracewell LLP; Constance G. Rhebergen; Kevin R. Tamm (57) ABSTRACT

Systems and methods for direct crude oil upgrading to hydrogen and chemicals including separating an inlet hydrocarbon stream into a light fraction and a heavy fraction comprising diesel boiling point temperature range material; producing from the light fraction syngas comprising $H_2$ and CO; reacting the CO produced; producing from the heavy fraction and separating $CO_2$, polymer grade ethylene, polymer grade propylene, $C_4$ compounds, cracking products, light cycle oils, and heavy cycle oils; collecting and purifying the $CO_2$ produced from the heavy fraction; processing the $C_4$ compounds to produce olefinic oligomerate and paraffinic raffinate; separating the cracking products; oligomerizing a light cut naphtha stream; hydrotreating an aromatic stream; hydrocracking the light cycle oils to produce a monoaromatics product stream; gasifying the heavy cycle oils; reacting the CO produced from gasifying the heavy cycle oils; collecting and purifying the $CO_2$; and processing and separating produced aromatic compounds into benzene and paraxylene.

36 Claims, 1 Drawing Sheet

(56) References Cited

U.S. PATENT DOCUMENTS

| | | |
|---|---|---|
| 6,743,961 B2 | 5/2004 | Powers |
| 6,979,757 B2 | 12/2005 | Powers |
| 7,019,187 B2 | 3/2006 | Powers |
| 7,374,664 B2 | 5/2008 | Powers |
| 7,396,449 B2 | 7/2008 | Powers |
| 7,404,889 B1 | 7/2008 | Powers |
| 7,419,584 B2 | 9/2008 | Stell et al. |
| 7,432,310 B2 * | 10/2008 | Steynberg ............ C07C 1/0485 208/108 |
| 7,550,642 B2 | 6/2009 | Powers |
| 7,744,747 B2 | 6/2010 | Halsey |
| 7,858,834 B2 | 12/2010 | Powers |
| 7,972,498 B2 | 7/2011 | Buchanan et al. |
| 9,096,806 B2 | 8/2015 | Abba et al. |
| 9,228,139 B2 | 1/2016 | Shafi et al. |
| 9,228,140 B2 | 1/2016 | Abba et al. |
| 9,228,141 B2 | 1/2016 | Sayed et al. |
| 9,255,230 B2 | 2/2016 | Shafi et al. |
| 9,279,088 B2 | 3/2016 | Shafi et al. |
| 9,284,497 B2 | 3/2016 | Bourane et al. |
| 9,284,501 B2 | 3/2016 | Sayed et al. |
| 9,284,502 B2 | 3/2016 | Bourane et al. |
| 9,296,961 B2 | 3/2016 | Shafi et al. |
| 9,382,486 B2 | 7/2016 | Bourane et al. |
| 10,407,629 B2 | 9/2019 | Oprins et al. |
| 2008/0011644 A1 | 1/2008 | Dean et al. |
| 2008/0011645 A1 | 1/2008 | Dean |
| 2008/0277314 A1 | 11/2008 | Halsey |
| 2008/0283445 A1 | 11/2008 | Powers |
| 2009/0050523 A1 | 2/2009 | Halsey |
| 2010/0158776 A1 | 6/2010 | Drnevich et al. |
| 2013/0067815 A1 | 3/2013 | Koseoglu et al. |
| 2013/0197285 A1 | 7/2013 | Shafi et al. |
| 2013/0197289 A1 | 7/2013 | Bourane et al. |
| 2013/0228496 A1 | 9/2013 | Bourane et al. |
| 2019/0203130 A1 | 7/2019 | Mukherjee |
| 2020/0399190 A1 * | 12/2020 | Behkish ................ B01J 29/703 |

* cited by examiner

SYSTEMS AND PROCESSES FOR DIRECT CRUDE OIL UPGRADING TO HYDROGEN AND CHEMICALS

BACKGROUND

Field

Embodiments of the disclosure relate to conversion and upgrading systems and processes for hydrocarbon fluids. In particular, certain embodiments of the disclosure relate to systems and processes for direct crude oil conversion and upgrading to petrochemical products not including gasoline or diesel and with reduced or eliminated carbon dioxide emissions.

Description of the Related Art

Ethylene, propylene, butenes, and butadiene, along with aromatic compounds such as benzene, toluene, and para-xylene represent some of the intermediates required in many systems and processes of the petrochemical industry. Necessary intermediate compounds are obtained through thermal cracking (steam pyrolysis) of petroleum gases and distillates such as naphtha, kerosene, and gas oil.

Some of these intermediate compounds are also produced through refinery fluidized catalytic cracking (FCC) processes in which classical heavy feedstocks such as gas oils or vacuum residues are converted to higher value products. One important source for propylene production is currently refinery propylene from FCC units.

Production of light olefins from FCC depends on several process variables including hydrocarbon feed type, operating conditions, and the type of catalyst(s). High Severity FCC (HS-FCC) systems including selective catalysts and enhanced hardware allow, in some cases, producing up to four times greater yield of propylene than traditional FCC units and greater conversion levels for a range of hydrocarbon feed streams. In addition to olefin streams such as propylene, ethylene and mixed butenes, other catalytic cracking reaction products include fuel gas, LPG, gasoline, light cycle oil, and heavy cycle oil.

Syngas, which includes hydrogen and carbon monoxide, can be produced from the gasification of heavy residue streams. Hydrogen can be produced from lighter hydrocarbon streams via several processes, including hydrocarbon steam reforming (HSR), partial oxidation (POX), and auto-thermal reforming (ATR). Hydrocarbon steam reforming involves the reaction of steam with hydrocarbons in the presence of a catalyst to produce hydrogen and CO.

Partial oxidation involves the reaction of oxygen with hydrocarbons to produce hydrogen and CO when the oxygen-to-hydrocarbon ratio is less than that required for total combustion to $CO_2$ and $H_2O$. Partial oxidation can be conducted with a catalyst (catalytic partial oxidation) or without a catalyst (non-catalytic partial oxidation). The reaction rates are greater for partial oxidation than for steam reforming, but the hydrogen yield per carbon in the hydrocarbon is lower. Non-catalytic partial oxidation requires reaction temperatures above about 1000° C. to achieve rapid reaction rates. Catalytic partial oxidation operates at lesser temperatures than the non-catalytic route. The lesser operating temperatures provide better control over the reaction, thus minimizing coke formation.

Auto-thermal reforming involves the reaction of oxygen, steam, and hydrocarbons to produce hydrogen and CO, and applies mechanisms of both partial oxidation and steam reforming.

High value chemicals can be obtained by processing carbon dioxide and carbon monoxide. For instance, carbon dioxide is utilized as a co-monomer in the polymerization of alkylene oxides, using, for example, double metal cyanide (DMC) catalysts, to produce polyols. Carbon monoxide can be utilized for the carbonylation of butadiene to produce adipic acid according to Equation 1. Phosgene, useful for preparing isocyanates, polycarbonates, and polyurethanes, is also produced by passing purified carbon monoxide and chlorine gas through a bed of porous activated carbon.

$$CH_2{=}CH{-}CH{=}CH_2 + 2CO + 2H_2O \rightarrow HO_2C(CH_2)_4CO_2H \qquad \text{Eq. 1}$$

Existing hydrocarbon conversion systems and processes do not allow for synergistic integration of processing units for the direct production of petrochemicals, not including gasoline and diesel, from a hydrocarbon feedstock comprising crude oil with reduced or eliminated carbon dioxide emissions.

SUMMARY

Applicant has recognized a need for systems and processes for the direct production of petrochemicals, not including gasoline and diesel as final products, from a hydrocarbon feedstock comprising crude oil with reduced or eliminated carbon dioxide emissions.

Embodiments of the disclosure relate to systems and processes for full conversion of crude oil or similar hydrocarbon feeds, for example, gas condensate, into upgraded petrochemicals and hydrogen. In one embodiment, crude oil is first split into a light fraction and a heavy fraction. The light fraction, including mostly naphtha boiling point temperature range material, is processed within a reformer to produce hydrogen. The heavy fraction, including diesel-plus boiling point temperature range material, is sent into a high-severity fluidized catalytic cracking (HS-FCC) process to produce light olefins and other liquid hydrocarbon streams that are further processed for aromatics production. Resulting heavy residue streams are processed within a gasifier to produce syngas, while carbon monoxide and carbon dioxide generated within the processes are separated and captured before being reacted with other hydrocarbons to produce additional useful chemical products.

Embodiments of the disclosure eliminate strict feedstock requirements for refining streams for on-purpose production of olefins, aromatics, and hydrogen while simultaneously minimizing or eliminating carbon dioxide and carbon monoxide emissions. A synergistic combination of hydrocarbon reforming and fluidized catalytic cracking enables direct cracking and conversion of crude oil in addition to or alternative to other hydrocarbon feeds such as condensates. Pretreatment such as fractionation of crude oil into several cuts is therefore not required in order to make available liquid hydrocarbon feeds for production of olefins, aromatics, and hydrogen, for example, pre-treatments such as producing naphtha or treating crude fractions such as vacuum gas oil to produce hydrowax.

Embodiments disclosed here advantageously maximize production of olefins, aromatic petrochemicals, and hydrogen from crude oil in addition to or alternative to other hydrocarbon sources such as gas condensates, while not producing gasoline or diesel as final products, or producing gasoline and diesel as final products combined at less than about 10 wt. % or less than about 5 wt. % of total produced products. Integrated configurations allow conversion of greater than about 80 wt. % or greater than about 90 wt. %, or greater than about 95 wt. % of crude oil into olefins, aromatic petrochemicals, hydrogen, and other useful upgraded chemicals with a minimized or eliminated $CO_2$ emissions footprint. Prior art systems and processes do not addresses direct cracking of crude oil fractions in a downflow reactor configuration to produce light olefins and $H_2$.

Therefore, disclosed here are methods for hydrocarbon separation and upgrading, one method including separating an inlet hydrocarbon stream into a light fraction comprising naphtha boiling point temperature range material and a heavy fraction comprising diesel boiling point temperature range material; producing from the light fraction syngas comprising $H_2$ and CO; reacting the CO produced from the light fraction via at least one reaction selected from the group consisting of: carbonylation, polymerization, and water-gas shift; producing from the heavy fraction and separating $CO_2$, polymer grade ethylene, polymer grade propylene, $C_4$ compounds, cracking products comprising naphtha boiling point temperature range products with olefins and aromatics, light cycle oils, and heavy cycle oils; collecting and purifying the $CO_2$ produced from the heavy fraction; processing the $C_4$ compounds to produce olefinic oligomerate and paraffinic raffinate, the paraffinic raffinate being used to produce hydrogen; separating the cracking products comprising naphtha boiling point temperature range products with olefins and aromatics into a light cut naphtha stream including $C_5$ and $C_6$ olefins and an aromatic stream comprising aromatic compounds; oligomerizing the light cut naphtha stream; hydrotreating the aromatic stream; hydrocracking the light cycle oils to produce a monoaromatics product stream; gasifying the heavy cycle oils to produce hydrogen, CO, and $CO_2$; reacting the CO produced from gasifying the heavy cycle oils via at least one reaction selected from the group consisting of: carbonylation, polymerization, and water-gas shift; collecting and purifying the $CO_2$ produced from gasifying the heavy cycle oils; and processing and separating produced aromatic compounds into benzene and para-xylene.

In some embodiments, the inlet hydrocarbon stream comprises at least one component selected from the group consisting of: crude oil and gas condensates. In other embodiments, gasoline and diesel are not final products of the method, or are produced at less than 10 wt. % or less than 5 wt. % of the final products of the method. In some embodiments, greater than about 90 wt. % by mass of the $CO_2$ and greater than about 90 wt. % by mass of the CO produced in the method are captured and further processed to other compounds.

Still other embodiments of the method further include the step of collecting and purifying $CO_2$ produced during the step of producing from the light fraction syngas comprising $H_2$ and CO. Some embodiments include the step of processing at least a portion of the produced $CO_2$ in at least one process selected from the group consisting of: dry reforming; steam reforming, and hydrogenation. Still other embodiments include the step of processing at least a portion of the produced $CO_2$ to produce at least one product selected from the group consisting of: a synthetic fuel; syngas comprising $H_2$ and CO; and olefins. In other embodiments, the step of separating the inlet hydrocarbon stream comprises the use of at least one unit selected from the group consisting of: a flash drum, a distillation-based separation unit, and a cyclonic vapor-liquid separation unit. In certain other embodiments, the steps of reacting the CO produced from the light fraction and reacting the CO produced from gasifying the heavy cycle oils include the step of producing adipic acid via carbonylation of butadiene.

In still other embodiments, the step of producing from the light fraction syngas comprising $H_2$ and CO comprises the use of at least one unit selected from the group consisting of: a steam reforming unit, a partial oxidation unit, and an auto-thermal reforming unit. In other embodiments, the step of producing from the heavy fraction is carried out using a high-severity fluidized catalytic cracking system comprising a downflow reactor. Still in other embodiments, a portion of $H_2$ produced in the method is used internally for hydrotreating. In other embodiments, the step of hydrocracking the light cycle oils includes hydrocracking and reforming reactions. Still other embodiments include the step of processing the monoaromatics product stream via trans-alkylation to convert toluene and $C_9$-$C_{11}$ aromatics into benzene and mixed xylenes. In some embodiments, the $CO_2$ produced from the heavy fraction includes $CO_2$ produced from coke burned in a regenerator of a catalytic cracking system. In still other embodiments, at least a portion of the heavy cycle oils produced from the heavy fraction is utilized to provide energy to the method.

In some embodiments of the method, the step of producing from the light fraction syngas comprising $H_2$ and CO further comprises producing hydrogen from at least one stream comprising saturated $C_1$ to $C_4$ compounds. In still other embodiments, the step of processing and separating produced aromatic compounds into benzene and para-xylene further produces heavy aromatics which are recycled to the step of hydrocracking the light cycle oils or gasifying the heavy cycle oils.

Additionally disclosed here are systems for hydrocarbon separation and upgrading, one system including an inlet hydrocarbon stream; a feed inlet splitter operable to separate the inlet hydrocarbon stream into a light fraction comprising naphtha boiling point temperature range material and a heavy fraction comprising diesel boiling point temperature range material; a hydrogen production unit operable to produce from the light fraction syngas comprising $H_2$ and CO; a carbon reaction unit operable to react the CO produced from the light fraction via at least one reaction selected from the group consisting of: carbonylation, polymerization, and water-gas shift; a high-severity fluidized catalytic cracking (HS-FCC) unit operable to produce from the heavy fraction $CO_2$, polymer grade ethylene, polymer grade propylene, $C_4$ compounds, cracking products comprising naphtha boiling point temperature range products with olefins and aromatics, light cycle oils, and heavy cycle oils; a $CO_2$ collection and processing unit operable to collect and purifying the $CO_2$ produced from the heavy fraction; an oligomerization unit operable to process the $C_4$ compounds to produce olefinic oligomerate and paraffinic raffinate, the paraffinic raffinate being used to produce hydrogen in the hydrogen production unit; a cracked naphtha splitter operable to separate the cracking products comprising naphtha boiling point temperature range products with olefins and aromatics into a light cut naphtha stream including $C_5$ and $C_6$ olefins and an aromatic stream comprising aromatic compounds, wherein the oligomerization unit is operable to oligomerize the light cut naphtha stream; a heavy naphtha selective hydrotreating unit operable to hydrotreat the aromatic stream; a cycle oils hydrocracker unit operable to hydrocrack the light cycle oils to produce a monoaromatics product stream; a gasifier unit operable to gasify the heavy cycle oils to produce hydrogen, CO, and $CO_2$, wherein the carbon reaction unit is operable to react the CO produced from gasifying the heavy cycle oils via at least one reaction selected from the group consisting of: carbonylation, polymerization, and water-gas shift, wherein the $CO_2$ collection and processing unit is operable to collect and purifying the $CO_2$ produced from gasifying the heavy cycle oils; and an aromatic extraction unit operable to process and separate produced aromatic compounds into benzene and para-xylene.

In some embodiments, the inlet hydrocarbon stream comprises at least one component selected from the group consisting of: crude oil and gas condensates. In other embodiments, gasoline and diesel are not final products of the system, or are less than about 5 wt. % or less than about 10 wt. % of the final products of the system. In yet other embodiments, greater than about 90 wt. % by mass of the $CO_2$ and greater than about 90 wt. % by mass of the CO produced in the system are captured and further processed to other compounds. Still in other embodiments, the $CO_2$ collection and processing unit is operable to collect and purify $CO_2$ produced from the hydrogen production unit. In certain embodiments, the system includes a $CO_2$ conversion unit operable to react $CO_2$ in at least one process selected from the group consisting of: dry reforming; steam reforming; and hydrogenation. In other embodiments, the system includes a $CO_2$ conversion unit operable to process at least a portion of the produced $CO_2$ to produce at least one product selected from the group consisting of: a synthetic fuel; syngas comprising $H_2$ and CO; and olefins.

Still in other embodiments of the system, the feed inlet splitter comprises at least one unit selected from the group consisting of: a flash drum, a distillation-based separation unit, and a cyclonic vapor-liquid separation unit. In some other embodiments, the carbon reaction unit is operable to react CO to produce adipic acid via carbonylation of butadiene. In some other embodiments, the hydrogen production unit includes at least one unit selected from the group consisting of: a steam reforming unit, a partial oxidation unit, and an auto-thermal reforming unit.

In some embodiments, the HS-FCC unit includes a downflow reactor. Still in other embodiments, a portion of $H_2$ produced in the system is used internally for hydrotreating. In yet other embodiments, the cycle oils hydrocracker unit includes hydrocracking and reforming reactions. Still in other embodiments, the aromatic extraction unit includes at least one unit selected from the group consisting of: a benzene extraction unit, a toluene plus $C_9$-$C_{11}$ trans-alkylation unit, a xylenes isomerization unit, and a para-xylene extraction unit. Some embodiments of the system include a catalyst regenerator to remove coke from catalyst. In other embodiments, at least a portion of the heavy cycle oils produced from the heavy fraction is utilized to provide energy to the system. Still in other embodiments, the hydrogen production unit includes a feed including saturated $C_1$ to $C_4$ compounds. And in yet other embodiments, heavy aromatics produced in the aromatic extraction unit are recycled to the cycle oils hydrocracker unit or the gasifier unit.

BRIEF DESCRIPTION OF THE DRAWINGS

These and other features, aspects, and advantages of the present disclosure will become better understood with regard to the following descriptions, claims, and accompanying drawing. It is to be noted, however, that the drawing illustrates only several embodiments of the disclosure and is therefore not to be considered limiting of the disclosure's scope as it can admit to other equally effective embodiments.

DETAILED DESCRIPTION

So that the manner in which the features and advantages of the embodiments of systems and methods for the direct conversion of crude oil to petrochemicals and $H_2$ not including gasoline and diesel with reduced or eliminated carbon dioxide emissions, may be understood in more detail, a more particular description of the embodiments of the present disclosure briefly summarized previously may be had by reference to the embodiments thereof, which are illustrated in the appended drawing, which forms a part of this specification. It is to be noted, however, that the drawing illustrates only various embodiments of the disclosure and is therefore not to be considered limiting of the present disclosure's scope, as it may include other effective embodiments as well.

Figure 1:
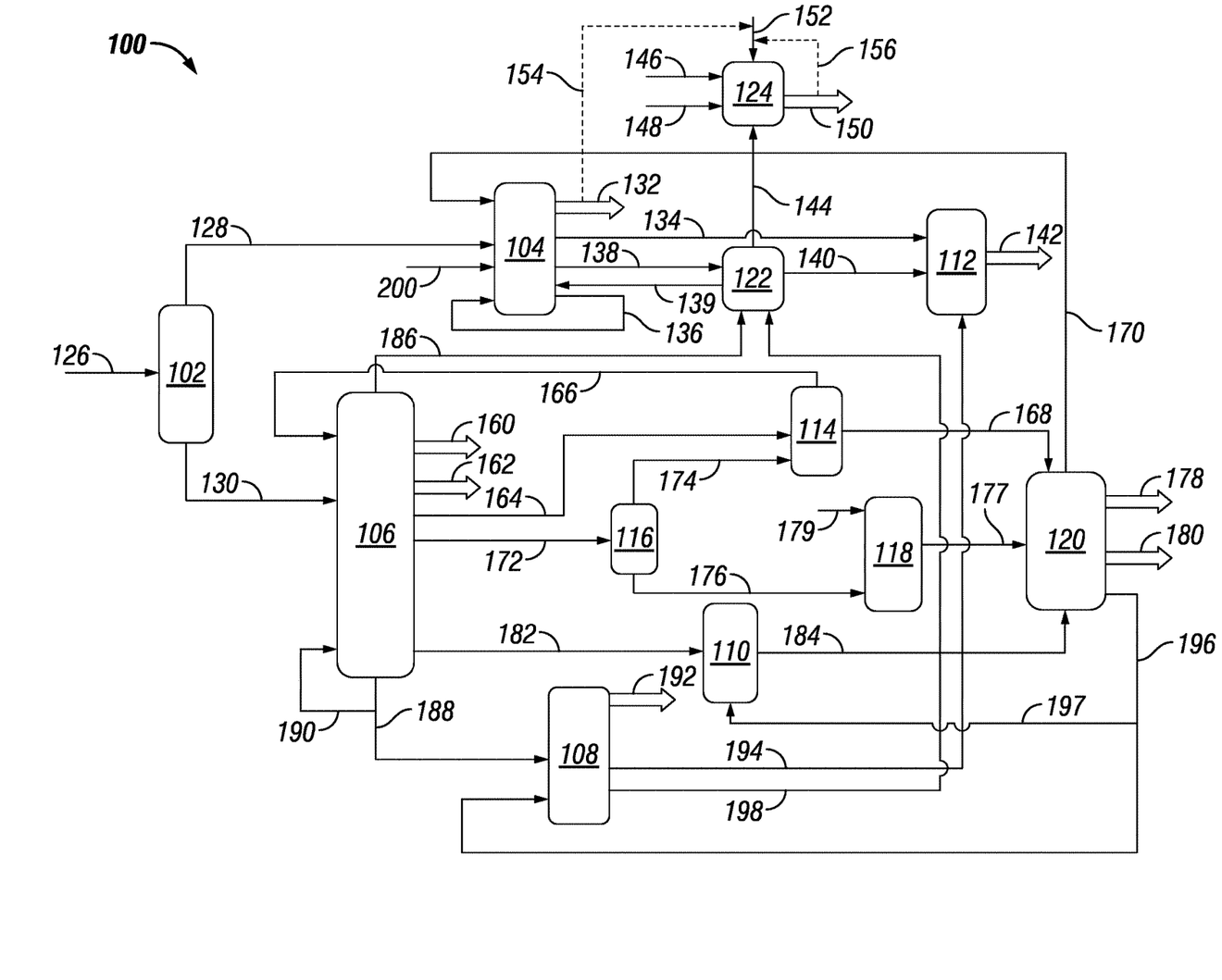
FIG. 1 is a schematic representing one embodiment of a system and process for the direct conversion of crude oil to petrochemicals and hydrogen, not including gasoline and diesel as final products, with reduced or eliminated carbon dioxide and carbon monoxide emissions.

Referring first to FIG. 1, a schematic is shown representing one embodiment of a system and process for the direct conversion of crude oil to petrochemicals and $H_2$ not including gasoline and diesel as final products, with reduced or eliminated carbon dioxide and carbon monoxide emissions. In the embodiment of FIG. 1, reduced emission crude oil processing system 100 includes a feed inlet splitter 102, a hydrogen production unit 104, a high-severity fluidized catalytic cracking (HS-FCC) unit 106, a gasifier unit 108, a cycle oils hydrocracker unit 110, a carbon reaction unit 112 to react, for example, carbon monoxide in addition to or alternative to carbon dioxide in a polymerization or carbonylation reaction, an oligomerization unit 114, a cracked naphtha splitter 116, a heavy naphtha selective hydrotreating unit 118, an aromatics extraction unit 120 (also referred to as an aromatics recovery unit), a $CO_2$ collection and processing unit 122, and a $CO_2$ conversion unit 124. Results of reduced emission crude oil processing system 100 include increased olefin, aromatic, and hydrogen production with increased $CO_2$ capture, conversion, and sequestration. Gasoline and diesel are not produced as final products in the embodiment of FIG. 1, and carbon monoxide and carbon dioxide are captured and processed rather than emitted to atmosphere.

Hydrocarbon feedstream 126 can include crude oil, such as whole crude oil, in addition to or alternative to a long boiling point range condensate, either or both of which can be routed without or in the absence of pretreatment (for example, hydroprocessing) to feed inlet splitter 102. Feed inlet splitter 102 separates hydrocarbon feedstream 126 to obtain a light fraction stream 128 and a heavy fraction stream 130. Feed inlet splitter 102 can include any one of or any combination of a flash drum, a distillation-based separation unit, or a cyclonic vapor-liquid separation unit, for example.

Light fraction stream 128 includes a light hydrocarbons fraction, and is mostly made up of naphtha boiling point temperature range material with a boiling point range below about 180° C., below about 250° C., or below about 370° C. Heavy fraction materials generally have a boiling point range greater than about 180° C., greater than about 250° C., or greater than about 370° C. In some embodiments, light fraction stream 128 includes more than about 50 wt. %, more than about 70 wt. %, more than about 90 wt. %, or more than 95 wt. % naphtha boiling point temperature range material.

Light fraction stream 128 proceeds to hydrogen production unit 104, which can include any one of or any combination of a steam reforming unit, a partial oxidation unit, and an auto-thermal reforming unit. Two products from hydrogen production unit 104 are hydrogen in hydrogen stream 132 and carbon monoxide in carbon monoxide stream 134 ($H_2$ and CO production being referred to as syngas). In some embodiments, hydrogen production unit 104 produces between about 40 mol. % and about 60 mol. %, for example about 50 mol. %, $H_2$, produces between about 30 mol. % and about 50 mol. %, for example about 40 mol. %, $CO_2$, produces between about 2 mol. % and about 3 mol. % CO, and produces between about 7 mol. % and about 8 mol. % $CH_4$. Hydrogen production unit 104 can include one or more reactor units operable to carry out water-gas shift on produced CO to produce additional hydrogen and $CO_2$.

Produced carbon monoxide in carbon monoxide stream 134 can be further separated from $H_2$ (for example by pressure swing adsorption) to then be reacted with water through the water-gas shift reaction to produce more hydrogen and carbon dioxide (not pictured) in addition to or alternative to routed to carbon reaction unit 112 to be used in a polymerization (for example to polycarbonyl) or carbonylation reaction, such as, for example, production of adipic acid via carbonylation of butadiene. Unconverted hydrocarbon stream 136 recycles unconverted naphtha-type hydrocarbon compounds to hydrogen production unit 104 to maximize syngas ($H_2$ and CO) production yields.

Hydrogen production unit 104 produces carbon dioxide as a byproduct in carbon dioxide stream 138, which proceeds to $CO_2$ collection and processing unit 122 for further purification and separation using $CO_2$ separation membranes, solvents, adsorbents, pressure swing, or any other purification operation or combination thereof. Separated and purified $CO_2$ in stream 139 from $CO_2$ collection and processing unit 122 can be recycled back to hydrogen production unit 104 and can be used with a steam reformer or dry reformer, for example, to further enhance hydrocarbon utilization. Separated and purified $CO_2$ can additionally or alternatively proceed through $CO_2$ stream 140 to carbon reaction unit 112 to produce chemicals, for example polyols, resulting in carbon sequestration chemical product stream 142. Separated and purified $CO_2$ can additionally or alternatively proceed to $CO_2$ conversion unit 124 via stream 144.

In some embodiments, two products from $CO_2$ collection and processing unit 122 include hydrogen and $CO_2$ with a small volume percent of CO, for examples less than 30 vol. %, less than 20 vol. %, or less than 10 vol. %. CO can be further treated as discussed with regard to carbon reaction unit 112, mostly via carbonylation reactions. $CO_2$ is ultimately routed to $CO_2$ conversion unit 124. Hydrogen from hydrogen production unit 104 is a product used for internal consumption in the process as well as exported as a product for potential use in transportation or other industries. $CO_2$ is primarily routed to $CO_2$ conversion unit 124, and CO is further converted through carbonylation reactions. $CO_2$ is utilized for value added product generation through polymerization or syngas generation through dry reforming reactions and further to dimethyl ether (DME) or olefin production.

$CO_2$ conversion unit 124 can convert $CO_2$ through reforming with lighter hydrocarbons, such as, for example, $CH_4$, $C_2H_6$, $C_3H_8$, in addition to or alternative to $C_4H_{10}$, entering via stream 146 in a dry reforming process, or $CO_2$ conversion unit 124 can convert $CO_2$ through steam reforming using steam entering via stream 148. Produced syngas in stream 150 ($H_2$ and CO) can be utilized as a feedstock for production of chemicals or synthetic fuels (not pictured). $CO_2$ can additionally or alternatively be hydrogenated in $CO_2$ conversion unit 124 using hydrogen stream 152, which can comprise a portion of hydrogen stream 132 diverted via stream 154, or could comprise renewable hydrogen from syngas from stream 150 diverted via stream 156. $CO_2$ conversion unit 124 can provide synthetic fuels as products (for example dimethyl ether in addition to or alternative to methanol via hydrogenation) in addition to or alternative to syngas (stream 150) with a reduced carbon foot print.

Heavy fraction stream 130 includes the heavy hydrocarbons fraction, composed mostly of diesel-plus boiling point temperature range material, which proceeds to HS-FCC unit 106. Heavy fraction stream 130 includes heavy components boiling above about 180° C., above about 220° C., or above about 370° C., for example. In some embodiments, heavy fraction stream 130 includes more than about 30 wt. %, more than about 50 wt. %, more than about 70 wt. %, more than about 90 wt. %, or more than 95 wt. % diesel-plus boiling point temperature range material boiling above about 180° C. In other embodiments not pictured, heavy fraction stream 130 can be split into two fractions: a diesel boiling point temperature range fraction and an atmospheric residue boiling point temperature range fraction, which are sent to two separate cracking reactors of a dual-downer cracking reactor system or a combination of riser and downer cracking reactors. HS-FCC unit 106 contains units to produce polymer grade ethylene in stream 160 and polymer grade propylene in stream 162. HS-FCC unit 106 can include a downflow reactor or series of downflow reactors.

In HS-FCC unit 106, more than about 20 wt. %, more than about 30 wt. %, or more than about 50 wt. % of the diesel-plus boiling point temperature range material can be converted to other useful chemicals. Example units suitable for HS-FCC 106 and suitable example temperatures, pressures, catalysts, and operating conditions are described, for example, in U.S. Pat. No. 9,290,705 to Bourane, et al.

Product stream 164 from HS-FCC unit 106 includes mixed $C_4$ compounds from the catalytic cracking process, which in the embodiment shown proceed to oligomerization unit 114. Oligomerization unit 114 produces at least two products: olefinic oligomerate that is routed back to HS-FCC unit 106 via stream 166 to maximize propylene yield in stream 162; and a rich paraffinic raffinate in stream 168, which proceeds via stream 170 to hydrogen production unit 104 after separation of aromatics in aromatics extraction unit 120. Mixed $C_4$ compounds include saturated normal $C_4$ compounds, iso-$C_4$ compounds, and olefinic 1-butene, isobutene, cis-butene, trans-butene, and traces of butadiene.

Suitable example oligomerization processes for unit 114 include, but are not limited to, the Polynaphtha™ indirect alkylation processes of Axens Solutions (headquartered in Rueil-Malmaison, France) for upgrading low value $C_3/C_4$ cuts into gasoline and middle distillates by oligomerization of light olefins contained in the $C_3/C_4$ cuts. Feedstock choices include propylene and mixed-butenes fractions (or combinations) present in $C_3$ and $C_4$ cuts from cracking processes including olefinic $C_3$ and $C_4$ cuts. Olefinic oligomerate and the rich paraffinic raffinate then include mostly $C_8$ olefinic and paraffinic compounds, for example at greater than 50 wt. %, greater than 75 wt. %, or greater than 90 wt. %. The Polynaphtha™ processes provide almost complete light olefins conversion, for example greater than 70%, greater than 80%, or greater than 90%.

Stream 172 includes catalytic cracking products from HS-FCC unit 106 in the naphtha boiling point temperature range and can be rich in both olefins and aromatics. In some embodiments, for example, stream 172 can include dry gas, mostly methane, between about 1 wt. % to about 5 wt. %; $C_2$-$C_4$ olefins at between about 30 wt. % to about 50 wt. %; naphtha at between about 30 wt. % to about 50 wt. %; light cycle oil at between about 2 wt. % to about 15 wt. %; and heavy cycle oil at between about 1 wt. % to about 5 wt. %. In embodiments described here, heavy cycle oils can include those cycle oils in a boiling range at 350° C. and greater, light cycle oils include those cycle oils in a boiling range from about 200° C. or 220° C. to about 350° C., and naphtha can include compounds boiling in the range between about 180° C. to about 200° C. or about 220° C.

Stream 172 proceeds to cracked naphtha splitter 116 for further separation into two streams. Light cut naphtha stream 174 includes light cut naphtha comprising $C_5$ and $C_6$ olefins, which are suitable for oligomerization and therefore are routed to oligomerization unit 114. Heavy aromatic stream 176 includes heavy aromatic compounds, which are suitable for extraction and ultimately the production of benzene in stream 178 and para-xylene in stream 180 from aromatics extraction unit 120. Heavy aromatic stream 176 is selectively hydrotreated in heavy naphtha selective hydrotreating unit 118 prior to aromatics extraction in aromatics extraction unit 120, because the aromatics extraction generally requires a feed low in nitrogen and sulfur concentrations. A hydrotreated naphtha stream 177 is produced by heavy naphtha selective hydrotreating unit 118. Hydrogen stream 179 can be supplied internally from hydrogen produced during syngas production in reduced emission crude oil processing system 100 and alternatively or additionally hydrogen in hydrogen stream 179 can be externally supplied.

HS-FCC unit 106 product stream 182 includes light cycle oil produced from HS-FCC unit 106 that proceeds to cycle oils hydrocracker unit 110. Cycle oils hydrocracker unit 110 includes a combination of hydrocracking and reforming reactions to maximize the amount of monoaromatics as product in stream 184, which is routed to aromatics extraction unit 120. Monoaromatics in stream 184 have been hydrotreated, and therefore stream 184 does not require further removal of sulfur and nitrogen as stream 176 does via heavy naphtha selective hydrotreating unit 118. In one embodiment, a configuration for cycle oils hydrocracker unit 110 includes a full-conversion hydrocracker followed by a catalytic reformer. Another suitable configuration includes a full conversion hydrocracker followed by dehydrogenation and trans-alkylation reaction units. In some embodiments, cycle oils hydrocracker unit 110 is integrated with aromatics extraction unit 120. Generally, aromatics extraction unit 120 will include a trans-alkylation unit to convert toluene and $C_9$-$C_{11}$ aromatics into benzene and mixed xylenes.

HS-FCC unit 106 product stream 186 includes $CO_2$ produced from burning coke generated in the cracking reactions. Coke is burned in a regenerator of the catalytic cracking system (not pictured) providing energy for feed vaporization, for maintaining operating temperature, and for the cracking reactions of HS-FCC unit 106, which are endothermic. Stream 186 proceeds to $CO_2$ collection and processing unit 122 for separation and purification, and then proceeds to carbon reaction unit 112 in addition to or alternative to $CO_2$ conversion unit 124 in addition to or alternative to hydrogen production unit 104 for further conversion to useful chemical products.

HS-FCC unit 106 product stream 188 includes the boiling point range material heavier than light cycle oil in stream 182, being referred to as heavy cycle oil and slurry. In some embodiments, all or a portion of stream 188 is recycled back to HS-FCC unit 106 for further processing via stream 190. In some embodiments, depending on feed characteristics and operating conditions of HS-FCC unit 106, coke formed during the cracking reactions will not provide enough energy to satisfy all the requirements of the process. In this case, stream 190 can provide an alternative source of heating energy. Stream 190 can be referred to in catalytic cracking systems as torch oil. Stream 190 can be continuously injected to a stripping stream section of HS-FCC unit 106.

In other embodiments, all or a portion of stream 188 is sent to gasifier unit 108 to be converted into syngas, including hydrogen stream 192 and carbon monoxide stream 194. Stream 196 includes resulting heavy aromatics from aromatics extraction unit 120 (for example $C_{9+}$, $C_{10+}$, $C_{11+}$, or $C_{12+}$ compounds) and is also routed to gasifier unit 108. Alternatively or additionally, all or a portion of stream 196 can be routed to cycle oils hydrocracker unit 110 via stream 197. Coke generated in gasifier unit 108 will be combusted to produce additional carbon dioxide in stream 198 that is separated and captured by $CO_2$ collection and processing unit 122, for example using absorption with amines in $CO_2$ collection and processing unit 122, and separated and purified $CO_2$ can proceed to carbon reaction unit 112 in addition to or alternative to $CO_2$ conversion unit 124 in addition to or alternative to hydrogen production unit 104 for further conversion to synthetic fuels or syngas. Similarly, carbon monoxide stream 194 proceeds to carbon reaction unit 112.

A gasifier or gasification unit can be an integrated unit that includes a reactor, an air separation unit, means for syngas quenching and cooling, a shift reactor, means for acid gas removal and recovery, and means for hydrogen recovery. The reaction zone can include a moving bed, fluidized bed, or entrained flow system. Gasifiers can be operated at a temperature of greater than about 800° C. and at a pressure of 10 bars or higher. Heavy residues from FCC systems and processes can be a suitable feed to be processed for syngas production, and coke generated in a gasifier can be combusted partially or totally to produce carbon monoxide or carbon dioxide.

Feed stream 200 to hydrogen production unit 104 includes any one of or any combination of the saturated $C_1$ to $C_4$ streams produced from other units (for example from HS-FCC unit 106, gasifier unit 108, cycle oils hydrocracker unit 110, oligomerization unit 114, cracked naphtha splitter 116, heavy naphtha selective hydrotreating unit 118, and aromatics extraction unit 120). Feed stream 200 can also contain hydrogen and methane. Prior to entering hydrogen production unit 104, feed stream 200 can proceed to a pressure swing adsorption (PSA) unit (not pictured). A PSA unit can separate hydrogen for use in, for example, heavy naphtha selective hydrotreating unit 118 in addition to or alternative to other units where hydrogen is required as an input. Separated methane proceeds to hydrogen production unit 104.

Heavy naphtha selective hydrotreating unit 118 treats stream 176 to remove contaminants and produce stream 177 proceeding to aromatics extraction unit 120. Sulfur and nitrogen contained in stream 176 are removed because they are contaminants for some of the catalysts used in aromatics extraction unit 120. Remaining olefins in stream 177 are fully hydrogenated, or otherwise removed, prior to aromatics extraction in aromatics extraction unit 120. Aromatics extraction unit 120 can include a selective hydrotreatment to preserve the content of the desired aromatics for recovery.

Cycle oils hydrocracker unit 110 includes a combination of hydrocracking and reforming reactions that maximize the amount of monoaromatics in stream 184, which is routed to aromatics extraction unit 120. If the hydrocracking product of cycle oils hydrocracker unit 110 is not a full conversion hydrocracking product and contains some products with a higher boiling range than naphtha, all or a portion of stream 184 can be routed and recycled to HS-FCC unit 106 in addition to or alternative to gasifier unit 108 (not pictured).

Aromatics extraction unit 120 carries out aromatics extraction with the production of benzene in stream 178 and para-xylene in stream 180. In some embodiments, aromatics extraction unit 120 can include any one of or any combination of a benzene extraction unit, a toluene plus $C_9$-$C_{11}$ trans-alkylation unit (de-alkylation in addition to or alternative to disproportionation), a xylenes isomerization unit (containing ethyl-benzene de-alkylation catalyst or not), and a para-xylene extraction unit. Byproducts of aromatics extraction unit 120 include rich paraffinic raffinate stream 170, which is routed to hydrogen production unit 104, and stream 196 including resulting heavy aromatics (for example $C_{9+}$, $C_{10+}$, $C_{11+}$, or $C_{12+}$ compounds), which is routed to gasifier unit 108 via stream 196 for syngas production in addition to or alternative to cycle oils hydrocracker unit 110 via stream 197 for hydrocracking.

Some of the streams and units needed for the configuration, but understood by those of ordinary skill in the art, have been omitted for clarity purposes. These streams and units can be considered as belonging to ancillary operations. For example, $H_2S$ is generally produced in cycle oils hydrocracker unit 110 and heavy naphtha selective hydrotreating unit 118 where hydro-treatment reactions take place. Cycle oils hydrocracker unit 110 and heavy naphtha selective hydrotreating unit 118 require hydrogen make-ups, which sources could be hydrogen production unit 104 in addition to or alternative to gasifier unit 108. Besides outside boundary limit units that are not pictured, there are others like amine recovery units, sour water strippers, and tail gas treatment units that can be applied where needed as understood by those of ordinary skill in the art. While technologies in FIG. 1 are represented as individual units, any unit may include multiple vessels, processes, and units working in series or parallel depending on varying inputs and desired products. In some embodiments, units pictures as separate in FIG. 1 may in fact be combined.

In other embodiments not pictured, hydrocarbon feedstream 126 can include a heavy crude oil that is first pretreated, for example, by any one of or any combination of hydroprocessing or supercritical water upgrading. Surprisingly and unexpectedly, embodiments of the disclosure provide for catalytic cracking of crude oil (in addition to or alternative to condensates) without any previous pretreatment (such as hydro-treatment) and with minimum splitting. There is little to no carbon footprint of the systems and processes for carbon monoxide and carbon dioxide, as carbon monoxide and carbon dioxide produced in the systems and processes are captured and converted, or routed for sequestration.

Produced syngas (including $H_2$ and CO) from reforming steps can be further reacted with $H_2O$ to produce additional $H_2$ and $CO_2$ through water-gas shift steps, in which CO reacts with steam to produce $H_2$ and $CO_2$. Produced hydrogen can be purified using pressure swing adsorption, a solvent system, or through hydrogen selective membranes to separate a pure hydrogen product. Separated $CO_2$ can be re-routed for various applications through conversion to high value chemicals, polymers, or for enhanced oil recovery application with further purification.

$CO_2$ can be recycled back to a reforming reactor, or $CO_2$ can be reacted with $CH_4$ through a dry reforming reaction to produce additional syngas with suitable $H_2$ to CO ratios for dimethyl ether production, which can subsequently be converted to olefins and other high value chemicals or petrochemical feedstocks.

Embodiments disclosed here eliminate the feedstock dependence of refining streams for on-purpose production of olefins, aromatics, and hydrogen. Systems and methods, for example reduced emission crude oil processing system 100, maximize the production of olefins and aromatics from crude oil and condensate sources while eliminating the final production of fuels such as naphtha, gasoline, and diesel. Carbon dioxide and carbon monoxide emissions are reduced or eliminated by separating, capturing, and converting them into valuable chemicals. $CO_2$-free hydrogen production is enabled using liquid hydrocarbon feeds in an optimized manner.

Synergistic combinations of hydrocarbon reforming and fluidized catalytic cracking enable direct cracking and conversion of crude oil and condensates. Fractionation of crude oil into several cuts is not required in embodiments of the present disclosure, for example to produce naphtha or to treat crude fractions such as vacuum gas oil to produce hydrowax, in order to make available liquid feeds for production of olefins, aromatics, and hydrogen.

Integrated configurations allow conversion of greater than about 80 wt. %, or greater than about 90 wt. %, or greater than about 95 wt. % of the crude oil into olefins, aromatic petrochemicals, other valuable chemicals, and hydrogen with reduced or eliminated $CO_2$ and CO emissions to the atmosphere.

Embodiments here disclose direct crude oil in addition to or alternative to condensate catalytic cracking and process integration between catalytic cracking in downflow reactors, reforming of hydrocarbons and gasification aimed at maximizing olefins, aromatics, and hydrogen production and minimization or elimination $CO_2$ emissions.

Crude oil feeds and other hydrocarbon feeds for processing in embodiments here do not require fractionation or upgrading before being processed for chemicals production. Final distillate products such as naphtha, kerosene, and gas oil obtained through costly and energy intensive refinery processing steps are not required as inputs here. Fuels such as gasoline and diesel are not co-produced as final products here with hydrogen, olefins, and aromatics.

Certain embodiments synergistically combine dual-downer FCC technology and process integration for hydrogen production and $CO_2$ minimization or elimination, and crude oils in addition to or alternative to condensates can be used as feedstocks to maximize olefin and hydrogen production, while minimizing $CO_2$ and fuel production.

The singular forms "a," "an," and "the" include plural referents, unless the context clearly dictates otherwise. The term "about" when used with respect to a value or range refers to values including plus and minus 5% of the given value or range.

One of ordinary skill in the art will understand that standard components such as pumps, compressors, temperature and pressure sensors, valves, and other components not shown in the drawings would be used in applications of the systems and methods of the present disclosure.

In the drawing and specification, there have been disclosed example embodiments of the present disclosure, and although specific terms are employed, the terms are used in a descriptive sense only and not for purposes of limitation. The embodiments of the present disclosure have been described in considerable detail with specific reference to these illustrated embodiments. It will be apparent, however, that various modifications and changes can be made within the spirit and scope of the disclosure as described in the foregoing specification, and such modifications and changes are to be considered equivalents and part of this disclosure.

The invention claimed is:

1. A method for hydrocarbon separation and upgrading, the method comprising the steps of:
    separating an inlet hydrocarbon stream into a light fraction comprising naphtha boiling point temperature range material and a heavy fraction comprising diesel boiling point temperature range material;
    producing from the light fraction syngas comprising $H_2$ and CO;
    reacting the CO produced from the light fraction via at least one reaction selected from the group consisting of: carbonylation, polymerization, and water-gas shift;
    producing from the heavy fraction and separating $CO_2$, polymer grade ethylene, polymer grade propylene, $C_4$ compounds, cracking products comprising naphtha boiling point temperature range products with olefins and aromatics, light cycle oils, and heavy cycle oils;
    collecting and purifying the $CO_2$ produced from the heavy fraction;
    processing the $C_4$ compounds to produce olefinic oligomerate and paraffinic raffinate, the paraffinic raffinate being used to produce hydrogen;
    separating the cracking products comprising naphtha boiling point temperature range products with olefins and aromatics into a light cut naphtha stream including $C_5$ and $C_6$ olefins and an aromatic stream comprising aromatic compounds;
    oligomerizing the light cut naphtha stream;
    hydrotreating the aromatic stream;
    hydrocracking the light cycle oils to produce a monoaromatics product stream;
    gasifying the heavy cycle oils to produce hydrogen, CO, and $CO_2$;
    reacting the CO produced from gasifying the heavy cycle oils via at least one reaction selected from the group consisting of: carbonylation, polymerization, and water-gas shift;
    collecting and purifying the $CO_2$ produced from gasifying the heavy cycle oils; and
    processing and separating produced aromatic compounds into benzene and paraxylene.

2. The method according to claim 1, wherein the inlet hydrocarbon stream comprises at least one component selected from the group consisting of: crude oil and gas condensates.

3. The method according to claim 1, wherein gasoline and diesel are not final products of the method.

4. The method according to claim 1, wherein greater than about 90 wt. % by mass of the $CO_2$ and greater than about 90 wt. % by mass of the CO produced in the method are captured and further processed to other compounds.

5. The method according to claim 1, further comprising the step of collecting and purifying $CO_2$ produced during the step of producing from the light fraction syngas comprising $H_2$ and CO.

6. The method according to claim 1, further comprising the step of processing at least a portion of the produced $CO_2$ in at least one process selected from the group consisting of: dry reforming; steam reforming, and hydrogenation.

7. The method according to claim 1, further comprising the step of processing at least a portion of the produced $CO_2$ to produce at least one product selected from the group consisting of: a synthetic fuel; syngas comprising $H_2$ and CO; and olefins.

8. The method according to claim 1, wherein the step of separating the inlet hydrocarbon stream comprises the use of at least one unit selected from the group consisting of: a flash drum, a distillation-based separation unit, and a cyclonic vapor-liquid separation unit.

9. The method according to claim 1, where the steps of reacting the CO produced from the light fraction and reacting the CO produced from gasifying the heavy cycle oils include the step of producing adipic acid via carbonylation of butadiene.

10. The method according to claim 1, wherein the step of producing from the light fraction syngas comprising $H_2$ and CO comprises the use of at least one unit selected from the group consisting of: a steam reforming unit, a partial oxidation unit, and an auto-thermal reforming unit.

11. The method according to claim 1, wherein the step of producing from the heavy fraction is carried out using a high-severity fluidized catalytic cracking system comprising a downflow reactor.

12. The method according to claim 1, wherein a portion of $H_2$ produced in the method is used internally for hydrotreating.

13. The method according to claim 1, wherein the step of hydrocracking the light cycle oils includes hydrocracking and reforming reactions.

14. The method according to claim 1, further comprising the step of processing the monoaromatics product stream via trans-alkylation to convert toluene and $C_9$-$C_{11}$ aromatics into benzene and mixed xylenes.

15. The method according to claim 1, wherein the $CO_2$ produced from the heavy fraction includes $CO_2$ produced from coke burned in a regenerator of a catalytic cracking system.

16. The method according to claim 1, wherein at least a portion of the heavy cycle oils produced from the heavy fraction is utilized to provide energy to the method.

17. The method according to claim 1, wherein the step of producing from the light fraction syngas comprising $H_2$ and CO further comprises producing hydrogen from at least one stream comprising saturated $C_1$ to $C_4$ compounds.

18. The method according to claim 1, wherein the step of processing and separating produced aromatic compounds into benzene and para-xylene further produces heavy aromatics which are recycled to the step of hydrocracking the light cycle oils or gasifying the heavy cycle oils.

19. A system for hydrocarbon separation and upgrading, the system comprising:
    an inlet hydrocarbon stream;
    a feed inlet splitter operable to separate the inlet hydrocarbon stream into a light fraction comprising naphtha boiling point temperature range material and a heavy fraction comprising diesel boiling point temperature range material;
    a hydrogen production unit operable to produce from the light fraction syngas comprising $H_2$ and CO;
    a carbon reaction unit operable to react the CO produced from the light fraction via at least one reaction selected from the group consisting of: carbonylation, polymerization, and water-gas shift;
    a high-severity fluidized catalytic cracking (HS-FCC) unit operable to produce from the heavy fraction $CO_2$, polymer grade ethylene, polymer grade propylene, $C_4$ compounds, cracking products comprising naphtha boiling point temperature range products with olefins and aromatics, light cycle oils, and heavy cycle oils;

a $CO_2$ collection and processing unit operable to collect and purifying the $CO_2$ produced from the heavy fraction;

an oligomerization unit operable to process the $C_4$ compounds to produce olefinic oligomerate and paraffinic raffinate, the paraffinic raffinate being used to produce hydrogen in the hydrogen production unit;

a cracked naphtha splitter operable to separate the cracking products comprising naphtha boiling point temperature range products with olefins and aromatics into a light cut naphtha stream including $C_5$ and $C_6$ olefins and an aromatic stream comprising aromatic compounds, wherein the oligomerization unit is operable to oligomerize the light cut naphtha stream;

a heavy naphtha selective hydrotreating unit operable to hydrotreat the aromatic stream;

a cycle oils hydrocracker unit operable to hydrocrack the light cycle oils to produce a monoaromatics product stream;

a gasifier unit operable to gasify the heavy cycle oils to produce hydrogen, CO, and $CO_2$, wherein the carbon reaction unit is operable to react the CO produced from gasifying the heavy cycle oils via at least one reaction selected from the group consisting of: carbonylation, polymerization, and water-gas shift, wherein the $CO_2$ collection and processing unit is operable to collect and purifying the $CO_2$ produced from gasifying the heavy cycle oils; and an aromatic extraction unit operable to process and separate produced aromatic compounds into benzene and para-xylene.

20. The system according to claim 19, wherein the inlet hydrocarbon stream comprises at least one component selected from the group consisting of: crude oil and gas condensates.

21. The system according to claim 19, wherein gasoline and diesel are not final products of the system.

22. The system according to claim 19, wherein greater than about 90 wt. % by mass of the $CO_2$ and greater than about 90 wt. % by mass of the CO produced in the system are captured and further processed to other compounds.

23. The system according to claim 19, wherein the $CO_2$ collection and processing unit is operable to collect and purify $CO_2$ produced from the hydrogen production unit.

24. The system according to claim 19, further comprising a $CO_2$ conversion unit operable to react $CO_2$ in at least one process selected from the group consisting of: dry reforming; steam reforming; and hydrogenation.

25. The system according to claim 19, further comprising a $CO_2$ conversion unit operable to process at least a portion of the produced $CO_2$ to produce at least one product selected from the group consisting of: a synthetic fuel; syngas comprising $H_2$ and CO; and olefins.

26. The system according to claim 19, where the feed inlet splitter comprises at least one unit selected from the group consisting of: a flash drum, a distillation-based separation unit, and a cyclonic vapor-liquid separation unit.

27. The system according to claim 19, where the carbon reaction unit is operable to react CO to produce adipic acid via carbonylation of butadiene.

28. The system according to claim 19, wherein the hydrogen production unit includes at least one unit selected from the group consisting of: a steam reforming unit, a partial oxidation unit, and an auto-thermal reforming unit.

29. The system according to claim 19, wherein the HS-FCC unit includes a downflow reactor.

30. The system according to claim 19, wherein a portion of $H_2$ produced in the system is used internally for hydrotreating.

31. The system according to claim 19, wherein the cycle oils hydrocracker unit includes hydrocracking and reforming reactions.

32. The system according to claim 19, where the aromatic extraction unit includes at least one unit selected from the group consisting of: a benzene extraction unit, a toluene plus $C_9$-$C_{11}$ trans-alkylation unit, a xylenes isomerization unit, and a paraxylene extraction unit.

33. The system according to claim 19, further comprising a catalyst regenerator to remove coke from catalyst.

34. The system according to claim 19, wherein at least a portion of the heavy cycle oils produced from the heavy fraction is utilized to provide energy to the system.

35. The system according to claim 19, wherein the hydrogen production unit includes a feed including saturated $C_1$ to $C_4$ compounds.

36. The system according to claim 19, wherein heavy aromatics produced in the aromatic extraction unit are recycled to the cycle oils hydrocracker unit or the gasifier unit.

* * * * *